(12) United States Patent
Matsui et al.

(10) Patent No.: US 6,255,081 B1
(45) Date of Patent: Jul. 3, 2001

(54) THERMOSTABLE FLAP ENDONUCLEASE DERIVED FROM HYPERTHERMOPHILE BACTERIUM BELONGING TO THE GENUS PYROCOCCUS

(75) Inventors: Ikuo Matsui; Kazuhiko Ishikawa; Yoshitsugu Kosugi; Eriko Matsui, all of Ibaraki; Satoko Kawasaki, Chiba, all of (JP)

(73) Assignee: Director - General of Agency of Industrial Science and Technology, Tokyo (JP)

( * ) Notice: Subject to any disclaimer, the term of this patent is extended or adjusted under 35 U.S.C. 154(b) by 0 days.

(21) Appl. No.: 09/175,973

(22) Filed: Oct. 21, 1998

Related U.S. Application Data

(62) Division of application No. 09/146,319, filed on Sep. 3, 1998.

(51) Int. Cl.⁷ ............... C12P 19/34; C12N 9/22; C12N 15/55
(52) U.S. Cl. ............ 435/91.1; 435/199; 435/252.3; 435/252.33; 435/320.1; 536/23.2
(58) Field of Search .................. 435/320.1, 194, 435/252.3, 252.33, 91.1; 536/23.2

(56) References Cited

U.S. PATENT DOCUMENTS

| | | | |
|---|---|---|---|
| 5,843,669 | * 12/1998 | Kaiser et al. | 435/6 |
| 5,846,717 | * 12/1998 | Brow et al. | 435/6 |
| 5,874,283 | * 2/1999 | Harrington et al. | 435/252.3 |

FOREIGN PATENT DOCUMENTS 9-239440 * 4/1997 (JP).

* cited by examiner

Primary Examiner—Charles L. Patterson, Jr.
(74) Attorney, Agent, or Firm—Foley & Lardner

(57) ABSTRACT

The present invention relates to a thermostable Flap endonuclease whose optimum temperature is 75° C. or more and DNA coding for (a) a protein consisting of the amino acid sequence shown in SEQ ID NO:2 or (b) a protein with Flap endonuclease activity, consisting of an amino acid sequence where in the amino acid sequence (a), one or more amino acids are deleted, substituted or added. According to the present invention, there is provided a thermostable Flap endonuclease whose optimum temperature for reaction is 75° C. or more. Further, this enzyme is thermally stable, so it becomes possible to develop new techniques of conducting artificial homologous recombination or genetic shuffling highly efficiently by coupling the enzyme reaction with PCR.

8 Claims, 2 Drawing Sheets

SEQUENCE LISTING

```
<160> NUMBER OF SEQ ID NOS: 7

<210> SEQ ID NO 1
<211> LENGTH: 1032
<212> TYPE: DNA
<213> ORGANISM: Pyrococcus horikoshii
<220> FEATURE:
<221> NAME/KEY: CDS
<222> LOCATION: (1)..(1029)

<400> SEQUENCE: 1
```

-continued

```
atg ggt gtt cct atc ggt gac ctc gtt ccg agg aag gag ata gat ctt      48
Met Gly Val Pro Ile Gly Asp Leu Val Pro Arg Lys Glu Ile Asp Leu
 1               5                  10                  15 gaa aat ctg tat gga aag aag ata gcg ata gat gcc cta aac gcc atc      96
Glu Asn Leu Tyr Gly Lys Lys Ile Ala Ile Asp Ala Leu Asn Ala Ile
             20                  25                  30 tat cag ttt tta tca acg ata aga cag agg gat gga aca cca ctt atg     144
Tyr Gln Phe Leu Ser Thr Ile Arg Gln Arg Asp Gly Thr Pro Leu Met
         35                  40                  45 gac tct aag ggt agg ata acc tct cat tta agt ggg ctc ttt tat aga     192
Asp Ser Lys Gly Arg Ile Thr Ser His Leu Ser Gly Leu Phe Tyr Arg
     50                  55                  60 acg ata aat cta atg gaa gcc ggt att aag ccg gcc tac gtc ttt gat     240
Thr Ile Asn Leu Met Glu Ala Gly Ile Lys Pro Ala Tyr Val Phe Asp
 65                  70                  75                  80 gga aag cct ccg gaa ttc aaa agg aag gag ctc gaa aaa agg agg gaa     288
Gly Lys Pro Pro Glu Phe Lys Arg Lys Glu Leu Glu Lys Arg Arg Glu
                 85                  90                  95 gct aga gaa gag gca gaa cta aaa tgg aaa gaa gct cta gcc aag gga     336
Ala Arg Glu Glu Ala Glu Leu Lys Trp Lys Glu Ala Leu Ala Lys Gly
            100                 105                 110 aac ctg gag gaa gct agg aaa tac gct caa agg gca act aag gtt aat     384
Asn Leu Glu Glu Ala Arg Lys Tyr Ala Gln Arg Ala Thr Lys Val Asn
        115                 120                 125 gaa atg cta atc gaa gat gca aag aag ctt ttg caa cta atg gga ata     432
Glu Met Leu Ile Glu Asp Ala Lys Lys Leu Leu Gln Leu Met Gly Ile
    130                 135                 140 cca ata att cag gct cca agt gaa gga gaa gcc caa gcg gca tac atg     480
Pro Ile Ile Gln Ala Pro Ser Glu Gly Glu Ala Gln Ala Ala Tyr Met
145                 150                 155                 160 gca agt aaa ggg gat gtc tac gcg tca gcg agt caa gat tat gat tca     528
Ala Ser Lys Gly Asp Val Tyr Ala Ser Ala Ser Gln Asp Tyr Asp Ser
                165                 170                 175 cta ctc ttt ggt gct cca agg ttg att agg aat ctg aca att acg gga     576
Leu Leu Phe Gly Ala Pro Arg Leu Ile Arg Asn Leu Thr Ile Thr Gly
            180                 185                 190 aaa aga aag atg cct ggg aaa gat gtt tac gtt gaa ata aag cca gag     624
Lys Arg Lys Met Pro Gly Lys Asp Val Tyr Val Glu Ile Lys Pro Glu
        195                 200                 205 tta gta gtt cta gat gag gta cta aaa gag ctt aag ata aca aga gaa     672
Leu Val Val Leu Asp Glu Val Leu Lys Glu Leu Lys Ile Thr Arg Glu
    210                 215                 220 aag ctt ata gaa ctt gca att ctg gtt ggg act gac tat aat cct ggg     720
Lys Leu Ile Glu Leu Ala Ile Leu Val Gly Thr Asp Tyr Asn Pro Gly
225                 230                 235                 240 ggc gta aag ggg ata gga cct aag aag gcc ctt gag att gta aga tat     768
Gly Val Lys Gly Ile Gly Pro Lys Lys Ala Leu Glu Ile Val Arg Tyr
                245                 250                 255 tca agg gat ccc cta gca aag ttc caa aga cag agc gat gtg gat ctt     816
Ser Arg Asp Pro Leu Ala Lys Phe Gln Arg Gln Ser Asp Val Asp Leu
            260                 265                 270 tac gct att aag gaa ttc ttc ctt aac cct cct gtc act aat gaa tac     864
Tyr Ala Ile Lys Glu Phe Phe Leu Asn Pro Pro Val Thr Asn Glu Tyr
        275                 280                 285 tcg ctt agt tgg aag gag cct gat gag gaa gga ata tta aaa ttc ctc     912
Ser Leu Ser Trp Lys Glu Pro Asp Glu Glu Gly Ile Leu Lys Phe Leu
    290                 295                 300 tgt gat gag cat aat ttt agc gaa gaa agg gta aaa aat ggg ata gaa     960
Cys Asp Glu His Asn Phe Ser Glu Glu Arg Val Lys Asn Gly Ile Glu
```

-continued

| 305 | | | 310 | | | 315 | | | 320 | | | | |
|---|---|---|---|---|---|---|---|---|---|---|---|---|---|
| aga | cta | aaa | aag | gcg | ata | aaa | gct | gga | aga | caa | tca | acg | ctt | gag | agt | 1008 |
| Arg | Leu | Lys | Lys | Ala | Ile | Lys | Ala | Gly | Arg | Gln | Ser | Thr | Leu | Glu | Ser |
| | | | 325 | | | | | 330 | | | | | 335 | | | tgg ttc gtt aaa aag aaa ccc taa  1032
Trp Phe Val Lys Lys Pro
            340

<210> SEQ ID NO 2
<211> LENGTH: 343
<212> TYPE: PRT
<213> ORGANISM: Pyrococcus horikoshii

<400> SEQUENCE: 2

Met Gly Val Pro Ile Gly Asp Leu Val Pro Arg Lys Glu Ile Asp Leu
 1               5                  10                  15

Glu Asn Leu Tyr Gly Lys Lys Ile Ala Ile Asp Ala Leu Asn Ala Ile
                20                  25                  30

Tyr Gln Phe Leu Ser Thr Ile Arg Gln Arg Asp Gly Thr Pro Leu Met
            35                  40                  45

Asp Ser Lys Gly Arg Ile Thr Ser His Leu Ser Gly Leu Phe Tyr Arg
        50                  55                  60

Thr Ile Asn Leu Met Glu Ala Gly Ile Lys Pro Ala Tyr Val Phe Asp
 65                  70                  75                  80

Gly Lys Pro Pro Glu Phe Lys Arg Lys Glu Leu Glu Lys Arg Arg Glu
                85                  90                  95

Ala Arg Glu Glu Ala Glu Leu Lys Trp Lys Glu Ala Leu Ala Lys Gly
            100                 105                 110

Asn Leu Glu Glu Ala Arg Lys Tyr Ala Gln Arg Ala Thr Lys Val Asn
        115                 120                 125

Glu Met Leu Ile Glu Asp Ala Lys Lys Leu Leu Gln Leu Met Gly Ile
    130                 135                 140

Pro Ile Ile Gln Ala Pro Ser Glu Gly Glu Ala Gln Ala Ala Tyr Met
145                 150                 155                 160

Ala Ser Lys Gly Asp Val Tyr Ala Ser Ala Ser Gln Asp Tyr Asp Ser
                165                 170                 175

Leu Leu Phe Gly Ala Pro Arg Leu Ile Arg Asn Leu Thr Ile Thr Gly
            180                 185                 190

Lys Arg Lys Met Pro Gly Lys Asp Val Tyr Val Glu Ile Lys Pro Glu
        195                 200                 205

Leu Val Val Leu Asp Glu Val Leu Lys Glu Leu Lys Ile Thr Arg Glu
    210                 215                 220

Lys Leu Ile Glu Leu Ala Ile Leu Val Gly Thr Asp Tyr Asn Pro Gly
225                 230                 235                 240

Gly Val Lys Gly Ile Gly Pro Lys Lys Ala Leu Glu Ile Val Arg Tyr
                245                 250                 255

Ser Arg Asp Pro Leu Ala Lys Phe Gln Arg Gln Ser Asp Val Asp Leu
            260                 265                 270

Tyr Ala Ile Lys Glu Phe Phe Leu Asn Pro Pro Val Thr Asn Glu Tyr
        275                 280                 285

Ser Leu Ser Trp Lys Glu Pro Asp Glu Glu Gly Ile Leu Lys Phe Leu
    290                 295                 300

Cys Asp Glu His Asn Phe Ser Glu Glu Arg Val Lys Asn Gly Ile Glu
305                 310                 315                 320

Arg Leu Lys Lys Ala Ile Lys Ala Gly Arg Gln Ser Thr Leu Glu Ser

-continued

```
                325                 330                 335
Trp Phe Val Lys Lys Lys Pro
                340
```

<210> SEQ ID NO 3
<211> LENGTH: 42
<212> TYPE: DNA
<213> ORGANISM: primer

<400> SEQUENCE: 3
gggaattcct gcagatcgca tatgggtgtt cctatcggtg ac                    42

<210> SEQ ID NO 4
<211> LENGTH: 42
<212> TYPE: DNA
<213> ORGANISM: primer

<400> SEQUENCE: 4
actaatcccg ggtacctcga ggctatagac tttagggttt ct                    42

<210> SEQ ID NO 5
<211> LENGTH: 30
<212> TYPE: DNA
<213> ORGANISM: Artificial Sequence
<220> FEATURE:
<223> OTHER INFORMATION: Description of Artificial Sequence:synthetic
      oligonucleotide used for the preparation of the
      Flap substrate

<400> SEQUENCE: 5
ggactctgcc tcaagacggt agtcaacgtg                                  30

<210> SEQ ID NO 6
<211> LENGTH: 16
<212> TYPE: DNA
<213> ORGANISM: Artificial Sequence
<220> FEATURE:
<223> OTHER INFORMATION: Description of Artificial Sequence:synthetic
      oligonucleotide used for the preparation of the
      Flap substrate

<400> SEQUENCE: 6
cacgttgact accgtc                                                 16

<210> SEQ ID NO 7
<211> LENGTH: 34
<212> TYPE: DNA
<213> ORGANISM: Artificial Sequence
<220> FEATURE:
<223> OTHER INFORMATION: Description of Artificial Sequence:synthetic
      oligonucleotide used for the preparation of the
      Flap substrate

<400> SEQUENCE: 7
gatgtcaagc agtcctaact ttgaggcaga gtcc                             34

THERMOSTABLE FLAP ENDONUCLEASE DERIVED FROM HYPERTHERMOPHILE BACTERIUM BELONGING TO THE GENUS PYROCOCCUS

This is a divisional application based on U.S. application Ser. No. 09/146,319 filed Sep. 3, 1998, the contents of which are incorporated by reference.

BACKGROUND OF THE INVENTION

1. Field of the Invention

The present invention relates to a thermostable Flap endonuclease effective for genetic recombination and genetic shuffling based on low homology, as well as to a gene thereof.

2. Description of the Prior Art

There are a method for random mutation of a broad region in a gene and a method for random mutation of a local region in a gene. In the former method, polymerase chain reaction (PCR) is applied such that a specific nucleotide is deleted to induce mutation at the time of replication of the target gene, and in the latter method, PCR using mixed primers is applied to mutate the target site. However, there is still no method for highly efficient induction of genetic recombination or genetic shuffling based on low homology in vitro. A speculative mechanism of genetic recombination and genetic shuffling in vivo is shown in FIG. 1. Step 1 of FIG. 1 shows formation of a single-stranded overhang by a 3'–5' exonuclease; step 2 shows formation of temporary nucleotide base pairs based on low homology; step 3 shows repair of the gap by DNA polymerase and formation of a Flap structure; step 4 shows removal of the Flap single strand by a Flap endonuclease; and step 5 shows ligation of nicks by a DNA ligase. However, the properties of the enzymes catalyzing the respective steps are not fully elucidated. The Flap endonuclease is an enzyme catalyzing step 4. As shown in FIG. 2, the Flap endonuclease specifically recognizes the Flap structure in DNA and cleaves the single strand (called Flap), and this enzyme is found in mammalian cells and yeast cells. Since its origin is organisms living at normal temperatures, this enzyme has poor thermostability and thus is not suitable for artificial genetic shuffling reaction, including PCR.

Because the conventional Flap endonuclease is unstable at high temperatures, it cannot be used to develop methods where genetic recombination or genetic shuffling based on low homology in vitro is induced at high temperatures. However, if a thermostable Flap endonuclease functioning stably at high temperatures can be obtained, it becomes possible to develop new techniques of conducting artificial homologous recombination or genetic shuffling highly efficiently by coupling the enzyme reaction with PCR. Accordingly, development of the thermostable Flap endonuclease stable at high temperature has long been desired.

SUMMARY OF THE INVENTION

Under these circumstances, the object of the present invention is to provide a novel thermostable Flap endonuclease and a gene thereof.

To achieve this object, the present inventors directed their attention to a hyperthermophile bacterium growing at 90 to 100° C., and as a result, a gene presumed to bring about the activity of the present enzyme was found in a gene sequence from the bacterium. Further, the enzyme was produced in E. coli by use of said gene, and it was confirmed that this enzyme is stable at high temperatures (75° C. or more) and exhibits structurally specific endonuclease activity. The present invention was thereby completed.

That is, the present invention relates to a thermostable Flap endonuclease whose optimum temperature is 75° C. or more.

Further, the present invention relates to a DNA coding for the following protein (a) or (b): (a) a protein consisting of the amino acid sequence shown in SEQ ID NO:2; and (b) a protein with Flap endonuclease activity, consisting of an amino acid sequence where in the amino acid sequence (a), one or more amino acids are deleted, substituted or added.

The DNA is a DNA specifically shown in SEQ ID NO:1.

The addition, deletion or substitution of amino acids can be effected using site-directed mutagenesis known in the art (see e.g. Nucleic Acid Research, Vol. 10, No. 20, pp. 6487–6500 (1982)). The number of one or more amino acids added, deleted or substituted is the number of amino acids which can be added, deleted or substituted by site-directed mutagenesis.

Further, the present invention relates to a recombinant vector comprising said DNA.

Further, the present invention relates to a transformant transformed with the recombinant vector comprising said DNA.

Further, the present invention relates to a process for producing a thermostable Flap endonuclease, which comprises culturing said transformant in a medium to produce the thermostable Flap endonuclease.

DETAILED DESCRIPTION OF THE INVENTION

Figure 1:
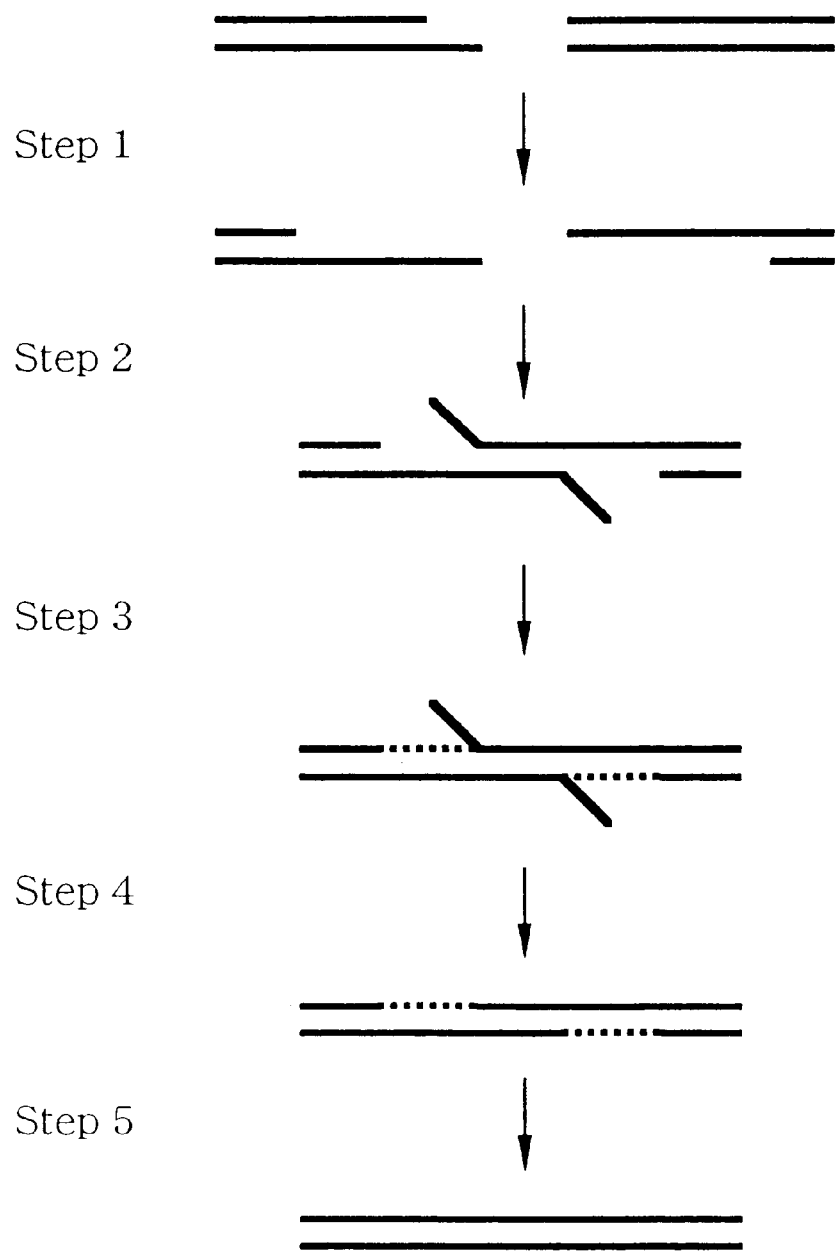
FIG. 1 shows a mechanism of homogeneous recombination and genetic shuffling in vivo in which the thermostable Flap endonuclease is involved. The Flap endonuclease catalyzes step 4.

Hereinafter, the present invention is described in detail.

The hyperthermophilic bacterium used in the present invention is sulfur-metabolizing thermophilic archaebacterium, *Pyrococcus horikoshii* JCM9974.

The thermostable Flap endonuclease of the present invention was obtained in the following manner. PCR was applied using chromosomal DNA as a template from *Pyrococcus horikoshii* JCM9974 and the upper and lower primers shown in Example 6, and a DNA fragment containing a Flap endonuclease gene was isolated.

This gene was inserted into protein expression plasmid pET 15b, then the resulting recombinant plasmid was integrated in *E. coli*, and the transformed *E. coli* was cultured in a medium to produce the present enzyme. The produced thermostable Flap endonuclease was isolated and purified by heat treatment and column chromatography. It was confirmed that the purified Flap endonuclease is a protein with a molecular weight of about 40,000 and is an enzyme which recognizes the Flap type DNA substrate shown in FIG. 2 and hydrolyzes a single-stranded portion (Flap portion) in an oligonucleotide.

The activity of the present enzyme did not decrease even after treatment of the enzyme at 95° C. for several hours in 50 mM phosphate buffer, pH 7.5 containing 1 M NaCl. Further, the optimum pH for activity was 6.0 to 8.0, and the optimum temperature was about 75° C. or more at pH 8.

EFFECT OF THE INVENTION

According to the present invention, there is provided a thermostable Flap endonuclease whose optimum temperature for reaction is 75° C. or more. Further, the present enzyme is thermally stable, so it becomes possible to develop new techniques of conducting artificial homologous recombination and genetic shuffling highly efficiently by coupling the enzyme reaction with PCR.

EXAMPLES

Hereinafter, the present invention is described in detail with reference to Examples, which, however, are not intended to limit the technical scope of the present invention.

Example 1
Culture of the Microorganism

*Pyrococcus horikoshii* JCM9974 was cultured in the following manner.

Dissolved in 1 L were 13.5 g sodium chloride, 4 g $Na_2SO_4$, 0.7 g KCl, 0.2 g $NaHCO_3$, 0.1 g KBr, 30 mg $H_3BO_3$, 10 g $MgCl_2 \cdot 6H_2O$, 1.5 g $CaCl_2$, 25 mg $SrCl_2$, 1.0 ml resazurin solution (0.2 g/L), 1.0 g yeast extract and 5 g Bacto-trypton, and this solution was adjusted to pH 6.8 and sterilized under pressure. Then, dry-sterilized elementary sulfur was added thereto at a concentration of 0.2%, and this medium was rendered anaerobic by saturation with argon, and *Pyrococcus horikoshii* JCM9974 was inoculated thereinto. Whether the medium became anaerobic or not was confirmed by failure of $Na_2S$ to cause the resazurin to turn pink in the culture solution upon addition of a $Na_2S$ solution. This culture solution was incubated at 95° C. for 2 to 4 days, and the resulting culture was harvested by centrifugation at 5000 rpm for 10 minutes to give 1 g of the microorganism.

Example 2
Preparation of Chromosomal DNA

Chromosomal DNA from *Pyrococcus horikoshii* JCM9974 was prepared in the following manner. The microorganism obtained (0.1 g) in Example 1 was washed twice with 10 mM Tris buffer (pH 7.5), 1 mM EDTA and enclosed in an InCert Agarose (FMC Co., Ltd.) block. This block was treated with 1% N-lauroylsarcosine and 1 mg/ml protease K, whereby the chromosomal DNA was separated and prepared in the Agarose block.

Example 3
Preparation of Library Clones Containing the Chromosomal DNA

The chromosomal DNA obtained in Example 2 was partially digested with restriction enzyme HindIII, and then a fragment of about 40-kb in length was prepared by agarose gel electrophoresis. This DNA fragment was ligated by T4 ligase to Bac vector pBAC108L (Ung-Jon Kim et al., Nucleic Acid Research, 20(5), 1083–1085 (1992)) and pFOSI (Ung-Jon Kim et al., Nucleic Acid Research, 20(5), 1083–1085 (1992)), both vectors having been completely digested with restriction enzyme HindII. If the former vector was used, the DNA after ligation was immediately introduced by electroporation into *E. coli*. If the latter vector pFOS1 was used, the DNA after ligation was packaged into λ-phage particles in vitro by GIGA Pack Gold (Stratagene) and these particles were infected into *E. coli* whereby the DNA was introduced into the *E. coli*. The resulting *E. coli* populations resistant to antibiotic chloramphenicol were used as BAC and Fosmid libraries respectively. From the libraries, clones suitable for covering the chromosome of *Pyrococcus horikoshii* JCM9974 were selected and alignment of the clones was conducted.

Example 4
Nucleotide Sequencing of each of the BAC and Fosmid Clones

Nucleotide sequencing of each of the aligned BAC and Fosmid clones was conducted in the following manner. The BAC or Fosmid clone DNA recovered from the *E. coli* was fragmented by ultrasonication, and 1- and 2-kb long DNA fragments were recovered by agarose gel electrophoresis. Shotgun clones with the fragments inserted into a HincII restriction enzyme site on plasmid vector pUC118, that is, 500 clones derived from each of the BAC and Fosmid clones, were prepared. The nucleotide sequence of each shotgun clone was determined by Automatic Nucleotide Sequence Reader 373 or 377 manufactured by Perkin Elmer, ABI. The nucleotide sequences obtained from the respective shotgun clones were linked and compiled by nucleotide sequence automatic linking software Sequencer to determine the whole nucleotide sequence of each of the BAC and Fosmid clones.

Example 5
Identification of the Flap Endonuclease Gene

The nucleotide sequence of each of the BAC and Fosmid clones determined above was analyzed by a large computer to identify a gene coding for the Flap endonuclease. The sequence of this gene is shown in SEQ ID NO:1. The amino acid sequence deduced from this nucleotide sequence is shown in SEQ ID NO:2.

Example 6
Construction of the Expression Plasmid

For the purpose of creating restriction enzyme sites (NdeI and XhoI) upstream and downstream from the structural gene, DNA primers were synthesized, and by PCR, the restriction enzyme sites were created in regions upstream and downstream from the gene.

Upper primer (SEQ ID NO:3):
5'-GGGAATTCCTGCAGATCGCATATGGGTGTTCCT-ATCGGTGAC-3'

Lower primer (SEQ ID NO:4):
5'-ACTAATCCCGGGTACCTCGAGGCTATAGACTTT-AGGGTTTCT-3'

After PCR, the product was completely digested (37° C., 2 hours) with the restriction enzymes (NdeI and XhoI) and the structural gene was then purified. pET-15b (Novagen) was cleaved with restriction enzymes NdeI and XhoI, then purified and ligated by T4 ligase to the above structural gene at 16° C. for 2 hours. A part of the ligated DNA was introduced into *E. coli*-XL 1-Blue MRF1 competent cells to give a transformant colony. The expression plasmid was purified from the resulting colony by the alkali method (Sambrook, J. et al., Molecular Cloning: A laboratory Manual, 2nd edn., Cold Spring Harbor Laboratory (1989)).

Example 7
Expression of the Recombinant Gene

*E. coli* competent cells (*E. coli* BL21 (DE3) available from Novagen) were fused and 0.1 ml cells were transferred to a Falcon tube. The expression plasmid solution (0.005 mL) was added to the cells, left on ice for 30 minutes, and heat-shocked at 42° C. for 30 seconds, and 0.9 mL SOC medium was added thereto, and the cells were cultured at 37° C. for 1 hour under shaking. Then, the cells were plated on a 2YT agar plate containing ampicillin and cultured at 37° C. overnight to give a transformant. This transformant has been deposited as FERM P-16389 on Aug. 18, 1997 with the National Institute of Bioscience and Human-Technology, Agency of Industrial Science and Technology, Japan.

This transformant was cultured in ampicillin-containing 2YT medium, 2L, until its absorbance at 600 nm reached 1, and then IPTG (isopropyl-β-D-thiogalactopyranoside) was added thereto, followed by culturing for further 6 hours. After culturing, the transformant was harvested by centrifugation (6,000 rpm, 20 minutes) to give 30 g of the microorganism.

Example 8
Purification of the Thermostable Enzyme

The harvested microorganism (30 g) was frozen at −20° C. and thawed, then alumina in an amount as twice as that of the microorganism and 1 mg DNase were added thereto, and the microorganism was disrupted, followed by adding a 5-fold excess amount of 10 mM Tris-HCl buffer (pH 8.0) to give a suspension. The resulting suspension was heated at 85° C. for 30 minutes and centrifuged (11,000 rpm, 20 minutes), and the supernatant was subjected to affinity chromatography on a Ni column (using Novagen, His-Bind metal chelation resin & His-Bind buffer kit). A fraction eluted with 60 mM imidazole was adsorbed onto a HiTrap SP (Pharmacia) and eluted with a concentration gradient of NaCl to give an active fraction. The resulting active fraction solution was further applied to a Hitrap Heparin column (Pharmacia) and eluted with a concentration gradient of NaCl to give 1 mg purified enzyme.

Example 9
Conditions for the Enzyme Reaction
(1) Synthetic Oligonucleotides

All oligonucleotides were synthesized by Grainer Japan Co., Ltd. The names and sequences of the respective oligonucleotides are as follows.

$F_{br}$ strand (SEQ ID NO:5):
5'-GGACTCTGCCTCAAGACGGTAGTCAACGTG-5'
$F_{adj}$ strand (SEQ ID NO:6): 5'-CTGCCATCAGTTGCAC-3'
Flap strand (SEQ ID NO:7):
5'-CCTGAGACGGAGTTTCAATCCTGACGAACTGTAG-5'

Figure 2:
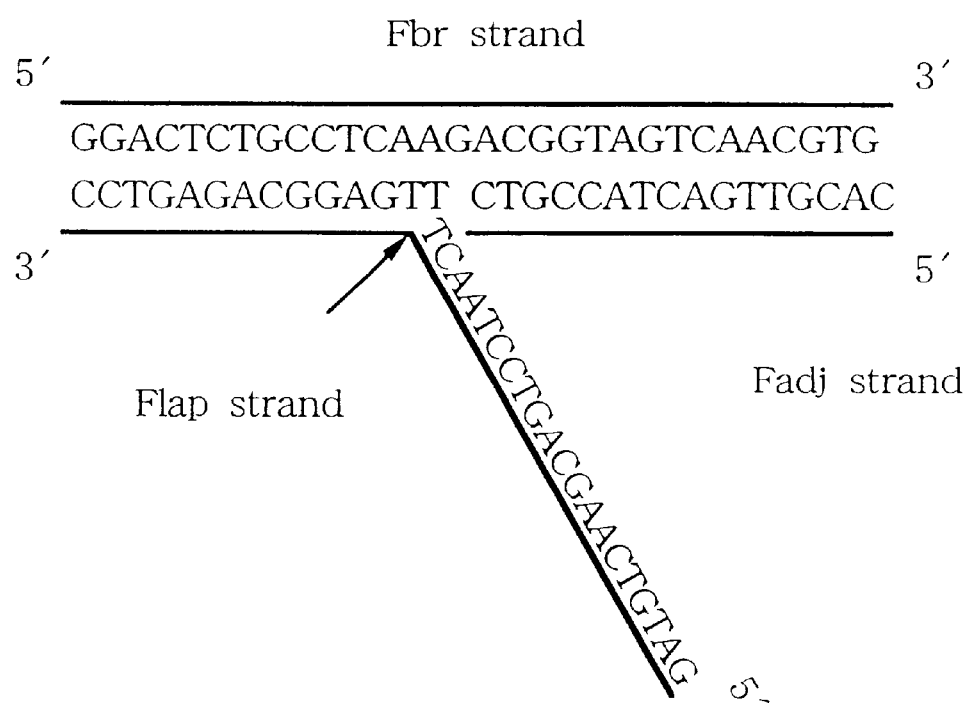
FIG. 2 shows one example of the DNA structure (SEQ ID NOS 5, 6, & 7, respectively) which can serve as a substrate for the Flap endonuclease. The single-stranded portion is called a Flap. The arrow indicates the site to be cleaved by this enzyme.

(2) Preparation of the Flap Substrate (FIG. 2)

The Flap strand was labeled at the 5'-terminal thereof with $^{32}P$ by means of $[\gamma-^{32}P]ATP$ and with $T_4$ polynucleotide kinase. The labeled Flap strand was boiled together with the $F_{br}$ and $F_{adj}$ strands in 20 mM Tris-HCl buffer, pH 7.4, 150 mM NaCl and then annealed by gradually lowering the temperature of the solution to 4° C.

(3) Flap endonuclease Activity

The $^{32}P$-labeled Flap substrate and the enzyme (400 fmol) were added to 15 ml of 50 mM Tris-HCl buffer (pH 8, 1.5 mM $MgCl_2$, 0.5 mM β-mercaptoethanol, 100 mg/ml bovine serum albumin) and reacted at 50 ° C. for 30 minutes. Then, 15 ml of 95% formamide, 10 mM EDTA and 1 mg/ml xylene cyanol were added to stop the enzyme reaction. Further, this reaction solution was heated at 95° C. for 5 minutes and electrophoresed at 2000 V for 2 hours in 15% polyacrylamide gel (16×45 cm) containing 7 M urea and 1×TBE (89 mM Tris, 89 mM boric acid, 2 mM EDTA, pH 8). The reaction product was imaged and quantified by Molecular Imager GS-525 (Bio-Rad). One unit activity is defined as the amount of the enzyme causing 1 fmol Flap substrate to be decomposed under usual conditions for measuring Flap endonuclease activity. Properties of the enzyme (1) Substrate Specificity The present enzyme does not act on double-stranded DNA or single-stranded DNA and has the endonuclease activity of cleaving off the single-stranded DNA (Flap) from the DNA structure shown in FIG. 2. In the substrate shown in FIG. 2, the arrow indicates the cleavage site from which the 20-mer single-stranded DNA is released. Further, the activity of this enzyme does not depend on the nucleotide sequence of DNA.

(2) Optimum pH

The optimum pH for enzyme activity was determined by measuring the initial rate of hydrolysis of the $^{32}P$-labeled Flap substrate (FIG. 2) by the enzyme at 50° C. in 50 mM sodium acetate buffer, 50 mM phosphate buffer and 50 mM borate buffer (pH 4 to 9), respectively. Because the maximum initial rate was achieved in the vicinity of pH 6.0 to 8.0, it was concluded that the optimum pH was 6.0 to 8.0.

(3) Optimum Temperature

A predetermined amount of the enzyme was added to 50 mM phosphate buffer, pH 8.0 containing 400 fmol $^{32}P$-labeled Flap substrate (FIG. 2) as the substrate and reacted for 30 minutes to examine its relative activity. The maximum activity (optimum temperature) was 75° C. or more.

(4) Thermostability

An aqueous solution containing the enzyme at a concentration of 0.1 mg/ml (50 mM phosphate buffer, pH 8.0, 1 M NaCl) was heated at 95° C. for 5 hours and then examined for its residual activity. The result indicated that the half-life of the activity was 5 hours. Further, a differential scanning colorimeter (DSC) was used to examine thermal denaturation. When 0.5 mg/ml of the enzyme solution (50 mM phosphate buffer, pH 8.0, 1 M NaCl) was measured at 0 to 125° C., it was revealed that the thermal denaturation temperature (Tm) is 103° C.

What is claimed is:

1. DNA coding for a protein comprising the amino acid sequence show in SEQ ID NO:2.

2. DNA comprising the nucleotide sequence show in SEQ ID NO:1.

3. A recombinant vector comprising the DNA of claim 1.

4. A transformant transformed with the recombinant vector of claim 3.

5. A process for producing a thermostable Flap endonuclease, which comprises culturing the transformant of claim 4 in a medium to produce the thermostable Flap endonuclease.

6. A recombinant vector comprising the DNA of claim 2.

7. DNA encoding a thermostable Flap endonuclease that is obtainable from a hyperthermophile bacterium belonging to the genus Pyrococcus, the optimum temperature of said endonuclease being 75° C. or more.

8. A method for treating nucleic acid in a high-temperature environment, comprising (1) providing a nucleic acid substrate with one or more cleavage structures and then, at a temperature in the range of at least 75° C., (2) reacting said nucleic acid substrate with a thermostable Flap endonuclease which has an optimum temperature in said range.

* * * * *